United States Patent
Yamanishi et al.

(10) Patent No.: US 11,058,348 B2
(45) Date of Patent: Jul. 13, 2021

(54) INFORMATION PROCESSING DEVICE, INFORMATION PROCESSING METHOD, AND COMPUTER-READABLE RECORDING MEDIUM RECORDING INFORMATION PROCESSING PROGRAM

(71) Applicant: PANASONIC INTELLECTUAL PROPERTY CORPORATION OF AMERICA, Torrance, CA (US)

(72) Inventors: Kouhei Yamanishi, Osaka (JP); Yoshikuni Sato, Osaka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 144 days.

(21) Appl. No.: 16/415,814

(22) Filed: May 17, 2019

(65) Prior Publication Data

US 2020/0029890 A1 Jan. 30, 2020

(30) Foreign Application Priority Data

Jul. 25, 2018 (JP) .............................. JP2018-139182

(51) Int. Cl.
| | |
|---|---|
| *A61B 5/00* | (2006.01) |
| *A61B 5/0205* | (2006.01) |
| *G01S 7/41* | (2006.01) |
| *A61B 5/113* | (2006.01) |
| *A61B 5/08* | (2006.01) |
| *A61B 5/024* | (2006.01) |

(52) U.S. Cl.
CPC .......... *A61B 5/4809* (2013.01); *A61B 5/0205* (2013.01); *A61B 5/113* (2013.01); *A61B 5/7275* (2013.01); *A61B 5/746* (2013.01); *G01S 7/415* (2013.01); *A61B 5/024* (2013.01); *A61B 5/08* (2013.01)

(58) Field of Classification Search
CPC ..... A61B 5/4809; A61B 5/0205; A61B 5/113; A61B 5/746
See application file for complete search history.

(56) References Cited

U.S. PATENT DOCUMENTS

| | | | | |
|---|---|---|---|---|
| 2009/0112069 | A1* | 4/2009 | Kanamori | ............. A61B 5/1118 600/300 |
| 2014/0371635 | A1* | 12/2014 | Shinar | .................. A61B 5/6892 600/595 |
| 2017/0135495 | A1* | 5/2017 | Hattori | ................. A61B 5/0022 |
| 2018/0064389 | A1 | 3/2018 | Takadama et al. | |

FOREIGN PATENT DOCUMENTS

WO 2016/148111 9/2016

* cited by examiner

*Primary Examiner* — Nadia A Mahmood
*Assistant Examiner* — Jessica L Mullins
(74) *Attorney, Agent, or Firm* — Greenblum & Bernstein, P.L.C.

(57) ABSTRACT

A falling asleep prediction device includes a biological data acquisition unit that acquires biological information on a subject, a falling asleep prediction unit that predicts that the subject falls asleep after predetermined time by using the biological information, and a notification processing unit that notifies that the subject falls asleep after the predetermined time.

15 Claims, 9 Drawing Sheets

FIG. 4

| TIME | HEARTBEAT I SIGNAL | HEARTBEAT Q SIGNAL | BREATHING I SIGNAL | BREATHING Q SIGNAL | BODY MOVEMENT I SIGNAL | BODY MOVEMENT Q SIGNAL |
|---|---|---|---|---|---|---|
| 18:00 | 35034 | 35010 | 33397 | 33400 | 33558 | 33504 |
| 18:01 | 35007 | 34842 | 33413 | 33476 | 33562 | 33532 |
| 18:02 | 35138 | 35110 | 33335 | 33445 | 33574 | 33554 |
| 18:03 | 34943 | 34686 | 33447 | 33455 | 33571 | 33484 |
| 18:04 | 34758 | 34844 | 33290 | 33394 | 33538 | 33504 |
| 18:05 | 34692 | 34746 | 33374 | 33417 | 33521 | 33482 |
| 18:06 | 35138 | 34996 | 33497 | 33398 | 33602 | 33503 |
| 18:07 | 34963 | 34825 | 33369 | 33390 | 33544 | 33529 |
| 18:08 | 34785 | 34832 | 33336 | 33419 | 33545 | 33488 |
| 18:09 | 35022 | 34949 | 33294 | 33401 | 33556 | 33535 |
| ... | ... | ... | ... | ... | ... | ... |

TIME

INFORMATION PROCESSING DEVICE, INFORMATION PROCESSING METHOD, AND COMPUTER-READABLE RECORDING MEDIUM RECORDING INFORMATION PROCESSING PROGRAM

FIELD OF THE INVENTION

The present disclosure relates to an information processing device, an information processing method, and a computer-readable recording medium recording an information processing program for predicting that a subject will fall asleep before the subject falls asleep by using biological information on the subject.

BACKGROUND ART

Conventionally, a method for estimating a sleep stage of a subject from heartbeat data is known. For example, a sleep stage estimation device described in WO 2016/148111 includes: an acquisition section to acquire biological data indicating a heartbeat wave; a parameter estimating section to estimate a parameter by using the biological data with respect to a mathematical formula defining a medium frequency component of the heartbeat wave by using the parameter; and a sleep stage estimating section to estimate a sleep stage from a value of the medium frequency component at any time point based on the mathematical formula to which the estimated parameter is applied. The parameter estimating section estimates the medium frequency component of the heartbeat wave from the biological data acquired from an unrestrained type sensor installed between a bed and a mattress on which the subject sleeps. The sleep stage estimating section estimates the sleep stage from the value of the medium frequency component.

Furthermore, WO 2016/148111 describes performing sleep monitoring of a nursing home resident by using the estimated sleep stage. For example, changing a diaper of a resident when the resident is deeply sleeping makes it possible to change the diaper without being clearly noticed by the resident.

However, the conventional technique, which enables estimation of the sleep stage of a subject after falling asleep, does not enable prediction of when the subject will fall asleep before falling asleep, and further improvement is needed.

SUMMARY OF THE INVENTION

The present disclosure has been made to solve the above problem, and an object of the present disclosure is to provide an information processing device, an information processing method, and a computer-readable recording medium recording an information processing program that enable prediction of when a subject will fall asleep before falling asleep.

An information processing device according to one aspect of the present disclosure includes an acquisition unit that acquires biological information on a subject, a prediction unit that predicts that the subject falls asleep after predetermined time by using the biological information, and a notification unit that notifies that the subject falls asleep after the predetermined time.

BRIEF DESCRIPTION OF THE DRAWINGS

FIG. 4 is a diagram showing one example of body movement data, breathing data, and heartbeat data according to the present embodiment;

Figure 1:
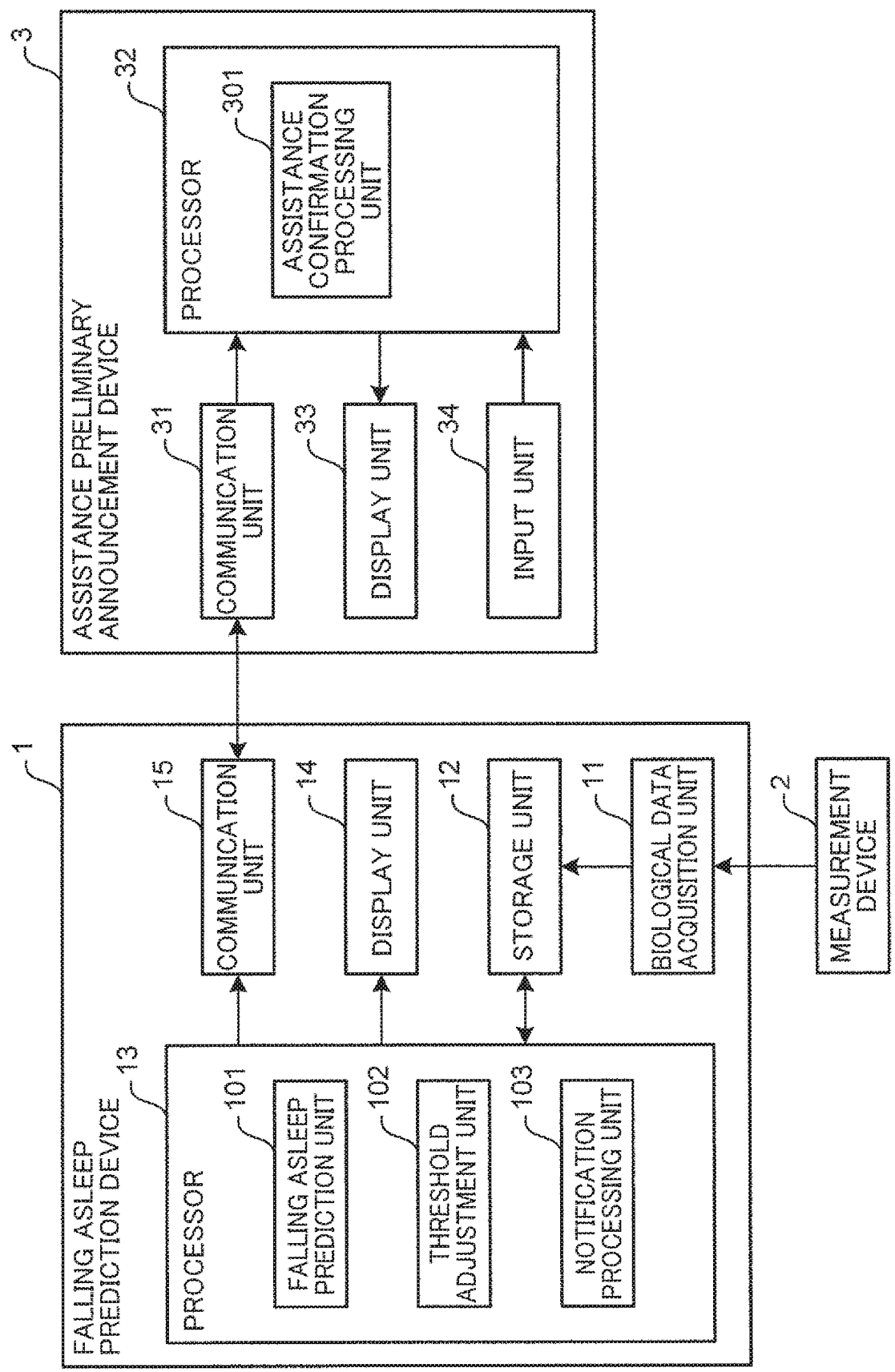
FIG. 1 is a diagram showing a configuration of a falling asleep prediction system according to an embodiment of the present disclosure.

DESCRIPTION OF EMBODIMENT (Underlying Knowledge Forming Basis of the Present Disclosure)

WO 2016/148111 assumes that a diaper is changed while a resident is sleeping, but as another assistance to the resident, there is assistance to be provided not while the resident is sleeping but immediately before the resident falls asleep, such as toothbrushing. In the present disclosure, assistance to be provided immediately before the resident falls asleep, such as toothbrushing, change of clothes, and medication, is referred to as falling asleep assistance. Actually, an assistant may not know timing when the resident falls asleep and may wake the resident by providing assistance after the resident has fallen asleep. According to WO 2016/148111, a sleep stage is estimated after a subject falls asleep, and thus it is not possible to predict when the subject will fall asleep before the subject falls asleep.

In order to solve the above problem, an information processing device according to one aspect of the present disclosure includes an acquisition unit that acquires biological information on a subject, a prediction unit that predicts that the subject falls asleep after predetermined time by using the biological information, and a notification unit that notifies that the subject falls asleep after the predetermined time.

With this configuration, it is predicted that the subject falls asleep after predetermined time and it is notified that the subject falls asleep after the predetermined time by using the biological information on the subject. Therefore, it is possible to predict when the subject falls asleep before falling asleep. For example, the subject is a person to be assisted, and the assistant who is notified that the subject falls asleep after the predetermined time can provide predetermined assistance to the subject before the subject falls asleep.

In the information processing device, the acquisition unit may acquire the biological information from a sensor that measures the biological information from the subject in a non-contact manner.

With this configuration, since the biological information is acquired from the sensor that measures the biological information from the subject in a non-contact manner, the subject does not need to wear the sensor, and the biological information can be acquired without preventing movement of the subject.

In the information processing device, the sensor may be a radio Doppler sensor. With this configuration, the biological information can be measured in a non-contact manner with the radio Doppler sensor.

In the information processing device, the biological information may include body movement data indicating body movement of the subject, breathing data indicating breathing of the subject, and heartbeat data indicating heartbeat of the subject.

With this configuration, it is possible to predict more accurately that the subject falls asleep after predetermined time, by using the body movement data indicating body movement of the subject, the breathing data indicating breathing of the subject, and the heartbeat data indicating heartbeat of the subject.

The information processing device may further include a storage unit configured to store a falling asleep prediction model constructed by machine learning using the biological information as an input value and a predicted value indicating probability that the subject falls asleep after the predetermined time as an output value. The prediction unit may determine whether the predicted value obtained by inputting the biological information into the falling asleep prediction model is larger than a threshold, and when it is determined that the predicted value is larger than the threshold, the prediction unit may determine that the subject falls asleep after the predetermined time.

With this configuration, it is possible to easily obtain the predicted value indicating the probability that the subject falls asleep after the predetermined time by inputting the biological information into the falling asleep prediction model constructed by machine learning, and it is possible to easily predict that the subject falls asleep after the predetermined time by comparing the predicted value with the threshold.

The information processing device may further include a threshold adjustment unit configured to adjust the threshold based on past falling asleep time tendency distribution of the subject.

With this configuration, since the threshold is adjusted based on the past falling asleep time tendency distribution of the subject, it is possible to accurately predict that the subject falls asleep after the predetermined time, by adjusting the threshold to be low when time after the predetermined time is time with high probability that the subject falls asleep in the past, and by adjusting the threshold to be high when time after the predetermined time is time with low probability that the subject falls asleep in the past.

In the information processing device, the notification unit may determine whether variation magnitude of past falling asleep time of the subject is equal to or less than a predetermined value, and when it is determined that the variation magnitude is equal to or less than the predetermined value, the notification unit may notify that the subject falls asleep after the predetermined time.

With this configuration, when it is determined that the variation magnitude of the past falling asleep time of the subject is equal to or less than the predetermined value, it is notified that the subject falls asleep after the predetermined time. This makes it possible to accurately notify that the subject falls asleep after the predetermined time.

In the information processing device, the subject may be a person to be assisted who receives predetermined assistance immediately before falling asleep, and when it is determined that the variation magnitude is larger than the predetermined value, the notification unit may transmit confirmation information for confirming with the subject whether to receive the predetermined assistance.

With this configuration, the subject is a person to be assisted who receives predetermined assistance immediately before falling asleep. When it is determined that the variation magnitude is larger than the predetermined value, the confirmation information is transmitted for confirming with the subject whether to receive the predetermined assistance.

When the past falling asleep time is not constant, a possibility of wrong prediction result that the subject falls asleep after the predetermined time increases. However, when the past falling asleep time is not constant, by confirming with the subject whether to receive the predetermined assistance, it is possible to accurately notify that the subject falls asleep after the predetermined time.

An information processing method according to another aspect of the present disclosure includes, by a computer: acquiring biological information on a subject; predicting that the subject falls asleep after predetermined time by using the biological information; and notifying that the subject falls asleep after the predetermined time.

With this configuration, it is predicted that the subject falls asleep after predetermined time and it is notified that the subject falls asleep after the predetermined time by using the biological information on the subject. Therefore, it is possible to predict when the subject falls asleep before falling asleep. For example, the subject is a person to be assisted, and the assistant who is notified that the subject falls asleep after the predetermined time can provide predetermined assistance to the subject before the subject falls asleep.

A computer-readable recording medium recording an information processing program according to another aspect of the present disclosure that causes a computer to function as: an acquisition unit configured to acquire biological information on a subject; a prediction unit configured to predict that the subject falls asleep after predetermined time by using the biological information; and a notification unit configured to notify that the subject falls asleep after the predetermined time.

With this configuration, it is predicted that the subject falls asleep after predetermined time and it is notified that the subject falls asleep after the predetermined time by using the biological information on the subject. Therefore, it is possible to predict when the subject falls asleep before falling asleep. For example, the subject is a person to be assisted, and the assistant who is notified that the subject falls asleep after the predetermined time can provide predetermined assistance to the subject before the subject falls asleep.

An embodiment of the present disclosure will be described below with reference to the accompanying drawings. Note that the following embodiment is one example embodying the present disclosure, and does not limit the technical scope of the present disclosure.

Embodiment

FIG. 1 is a diagram showing a configuration of a falling asleep prediction system according to an embodiment of the present disclosure.

The falling asleep prediction system shown in FIG. 1 includes a falling asleep prediction device 1, a measurement device 2, and an assistance preliminary announcement device 3.

The falling asleep prediction device 1 predicts falling asleep of a person who is present in a target area. In the present embodiment, the target area is, for example, an area within a single room that is provided in facilities such as a nursing home or residences with health and welfare services for the elderly and used by a prediction subject. If the target area is an area within a single room of a nursing home or residences with health and welfare services for the elderly, the prediction subject is a person to be assisted who lives in the single room. Alternatively, if the target area is an area within a hospital room of a hospital, the prediction subject is a patient who is hospitalized in the hospital room for medical treatment or other purposes. For example, in the nursing home or residences with health and welfare services for the elderly, a person to be assisted is present who needs assistance before falling asleep, such as toothbrushing, change of clothes, and medication. In order to smoothly provide falling asleep assistance without waking the person to be assisted who has already fallen asleep, an assistant desires to know in advance timing when the person to be assisted falls asleep. The falling asleep prediction device 1 of the present embodiment predicts falling asleep of the subject and notifies the assistant in advance.

The falling asleep prediction device 1 is, for example, a personal computer or a tablet computer, and is used by the assistant who assists the subject.

The assistance preliminary announcement device 3 is, for example, a personal computer, a smart phone, or a tablet computer, and is used by the subject.

The falling asleep prediction device 1 is connected to the assistance preliminary announcement device 3 communicatively with each other via a network. Note that the network is, for example, the Internet.

The measurement device 2 measures a physical quantity with a value changing according to presence and operation of a person in the target area. In the present embodiment, the measurement device 2 measures the physical quantity with a value changing according to presence and operation of a person in the target area in a non-contact manner. The measurement device 2 includes a sensor that measures biological data (biological information) from the subject in a non-contact manner. The measurement device 2 transmits the measured biological data to the falling asleep prediction device 1.

The falling asleep prediction device 1 includes a biological data acquisition unit 11, a storage unit 12, a processor 13, a display unit 14, and a communication unit 15.

The processor 13 includes a falling asleep prediction unit 101, a threshold adjustment unit 102, and a notification processing unit 103.

The biological data acquisition unit 11 acquires the biological data of the subject (biological information). The biological data acquisition unit 11 acquires the biological data regarding body movement, heartbeat, and breathing of the subject from the measurement device 2. The biological data includes body movement data indicating the body movement of the subject, breathing data indicating the breathing of the subject, and heartbeat data indicating the heartbeat of the subject.

The storage unit 12 stores the biological data acquired by the biological data acquisition unit 11. The storage unit 12 also stores data such as a program or a parameter as necessary.

The falling asleep prediction unit 101 predicts falling asleep of the subject by using the biological data stored in the storage unit 12. The falling asleep prediction unit 101 predicts that the subject will fall asleep after predetermined time by using the biological data acquired by the biological data acquisition unit 11. The predetermined time is, for example, 30 minutes. That is, the falling asleep prediction unit 101 predicts that the subject will fall asleep in 30 minutes by using the biological data acquired by the biological data acquisition unit 11. Note that the predetermined time is not limited to 30 minutes.

Also, the storage unit 12 stores a falling asleep prediction model constructed by machine learning using the biological data as an input value and a predicted value indicating probability that the subject will fall asleep after the predetermined time as an output value. The falling asleep prediction unit 101 determines whether the predicted value obtained by inputting the biological data into the falling asleep prediction model is larger than a threshold. Upon determination that the predicted value is larger than the threshold, the falling asleep prediction unit 101 determines that the subject will fall asleep after the predetermined time. Note that in the present embodiment, the subject is a person to be assisted who receives predetermined assistance immediately before falling asleep.

The threshold adjustment unit 102 adjusts the threshold to be used by the falling asleep prediction unit 101 based on past falling asleep time tendency distribution of the subject.

When the falling asleep prediction unit 101 detects that the subject will fall asleep after the predetermined time, the notification processing unit 103 performs notification processing to the subject or the assistant. The notification processing unit 103 notifies that the subject will fall asleep after the predetermined time.

More specifically, the notification processing unit 103 determines whether variation magnitude of the past falling asleep time of the subject is equal to or less than a predetermined value. Upon determination that the variation magnitude is equal to or less than the predetermined value, the notification processing unit 103 generates notification information for notifying that the subject will fall asleep after the predetermined time, and outputs the generated notification information to the display unit 14. Alternatively, upon determination that the variation magnitude is larger than the predetermined value, the notification processing unit 103 generates confirmation information for confirming with the subject whether to receive predetermined assistance, and transmits the generated confirmation information to the assistance preliminary announcement device 3.

The display unit 14 is, for example, a liquid crystal display, and displays the notification information generated by the notification processing unit 103. The assistant recognizes that the subject will fall asleep after the predetermined time by looking at the notification information displayed on the display unit 14. Then, before the subject falls asleep, the assistant provides the predetermined assistance.

The communication unit 15 transmits the confirmation information for confirming with the subject whether to receive the predetermined assistance to the assistance preliminary announcement device 3. Also, the communication unit 15 receives response information indicating whether the subject receives the predetermined assistance from the assistance preliminary announcement device 3.

That is, the falling asleep prediction device 1 plays an auxiliary role for the assistant to provide falling asleep assistance by detecting and notifying a falling asleep sign of the subject based on the biological data acquired from the measurement device 2.

Note that in the present embodiment, the display unit 14 displays that the subject falls asleep after the predetermined time, but the present disclosure is not particularly limited to this example. The falling asleep prediction device 1 may include a speaker, which may notify by voice that the subject falls asleep after the predetermined time.

The assistance preliminary announcement device 3 includes a communication unit 31, a processor 32, a display unit 33, and an input unit 34.

The communication unit 31 receives, from the falling asleep prediction device 1, the confirmation information for confirming with the subject whether to receive the predetermined assistance.

The processor 32 includes an assistance confirmation processing unit 301. The assistance confirmation processing unit 301 generates a confirmation screen for confirming with the subject whether to receive the predetermined assistance, and displays the generated confirmation screen on the display unit 33.

The display unit 33 is, for example, a liquid crystal display, and displays the confirmation screen for confirming with the subject whether to receive the predetermined assistance.

The input unit 34 is, for example, a touch panel, and receives input by the subject about whether to receive the predetermined assistance. For example, the confirmation screen displays a text for confirming with the subject whether to receive the predetermined assistance, a first button to be pressed when the subject receives the predetermined assistance, and a second button to be pressed when the subject does not receive the predetermined assistance. The subject presses the first button when receiving the predetermined assistance, or presses the second button when not receiving the predetermined assistance.

Based on information that is input through the input unit 34 indicating whether to receive the predetermined assistance, the assistance confirmation processing unit 301 generates the response information indicating whether the subject receives the predetermined assistance, and then transmits the generated response information to the falling asleep prediction device 1. The communication unit 31 transmits the response information indicating whether the subject receives the predetermined assistance to the falling asleep prediction device 1.

Hereinafter, details of the falling asleep prediction system according to the present embodiment will be described.

Hereinafter, an example in which target space is set within a single room of residences with health and welfare services for the elderly will be described. The subject in this case is a resident of the single room.

The falling asleep prediction device 1 predicts falling asleep of the subject and notifies the assistant or other persons.

The measurement device 2 includes, for example, a radio Doppler sensor and a signal processing unit. The Doppler sensor transmits, for example, a microwave-band electromagnetic wave to the target area at predetermined time intervals (for example, at one-second intervals). The Doppler sensor receives a reflected wave reflected by a person or the like who is present in the target area. The signal processing unit of the measurement device 2 performs signal processing on the reflected wave received by the Doppler sensor, and generates body movement data indicating body movement of the person who is present in the target area. Also, the signal processing unit of the measurement device 2 generates heartbeat data indicating body movement generated by heartbeat by filtering the body movement data indicating the body movement of the person and extracting a frequency component of the body movement generated by the heartbeat. Also, the signal processing unit of the measurement device 2 generates breathing data indicating body movement generated by breathing by filtering the body movement data indicating the body movement of the person and extracting a frequency component of the body movement generated by the breathing.

The measurement device 2 outputs, to the falling asleep prediction device 1, the body movement data indicating the body movement of the person who is present in the target area, the heartbeat data indicating the body movement generated by the heartbeat, and the breathing data indicating the body movement generated by the breathing. Note that the measurement device 2 includes, for example, a wireless communication unit in conformity to Bluetooth (registered trademark) or other standards, and wirelessly transmits the measured biological data to the falling asleep prediction device 1.

The sensor included in the measurement device 2 is not limited to the radio Doppler sensor but may be an ultrasonic Doppler sensor that transmits ultrasonic waves. The communication between the measurement device 2 and the falling asleep prediction device 1 is not limited to wireless communication but may be cable communication. Also, the measurement device 2, which measures the biological data such as the body movement data in a non-contact manner, does not prevent person's movement.

Note that the measurement device 2 may include, for example, a wearable sensor that can be worn on an arm and may measure the biological data in contact with the subject.

In the present embodiment, the falling asleep prediction device 1 is implemented, for example, by a personal computer provided in a station for the assistant in facilities such as a nursing home or residences with health and welfare services for the elderly.

The biological data acquisition unit 11 includes, for example, a wireless communication unit in conformity to Bluetooth (registered trademark) or other standards. The biological data acquisition unit 11 acquires the body movement data, the heartbeat data, and the breathing data from the measurement device 2 by wirelessly communicating with the measurement device 2 regularly or irregularly. After acquiring the body movement data, the heartbeat data, and the breathing data from the measurement device 2, the biological data acquisition unit 11 outputs the acquired body movement data, the heartbeat data, and the breathing data to the storage unit 12.

The storage unit 12 includes, for example, an electrically rewritable nonvolatile memory such as an electrically erasable programmable read only memory (EEPROM), and a volatile memory such as a random access memory (RAM). The storage unit 12 stores the body movement data, the heartbeat data, the breathing data, and other data acquired by the biological data acquisition unit 11.

Functions of the falling asleep prediction unit 101, the threshold adjustment unit 102, and the notification processing unit 103 are implemented by the processor 13 executing a predetermined program. The program may be recorded in a memory or the storage unit 12 in advance, or may be provided through electric telecommunication lines such as the Internet or through recording in a non-transitory recording medium such as a memory card.

The storage unit 12 stores the falling asleep prediction model. The falling asleep prediction model outputs the predicted value by using the biological data acquired before predetermined timing. In the present embodiment, as one example, the predicted value is an index that is represented with a real number between 0 and 1 inclusive, and represents probability that the subject falls asleep within 30 minutes from the current time. In the present embodiment, the falling asleep prediction model is constructed in advance by machine learning that uses, as input data, the biological data in a period from 30 minutes before the falling asleep time to time immediately before falling asleep recorded in the past, and the biological data in a period from 18:00 to 30 minutes before the falling asleep time. In the present embodiment, input data at time within 30 minutes before the subject falls asleep is called positive data with the falling asleep sign, whereas input data at time before time that is 30 minutes before the subject falls asleep is called negative data without the falling asleep sign.

The falling asleep prediction unit 101 inputs the biological data acquired by the biological data acquisition unit 11 into the falling asleep prediction model, and obtains the predicted value that is output from the falling asleep prediction model.

The threshold adjustment unit 102 calculates a threshold for comparison with the predicted value that is output by the falling asleep prediction model. The threshold adjustment unit 102 calculates the threshold to be used for falling asleep prediction processing to be described later by using a first threshold TH1, a second threshold TH2, and the falling asleep time tendency distribution.

In the present embodiment, as a determination result of the falling asleep prediction unit 101, a case where the predicted value exceeds the threshold is called positive, and a case where the predicted value is less than the threshold is called negative. Falsely determining input positive data to be negative is called false negative, whereas falsely determining input negative data to be positive is called false positive. The false negative rate is a proportion of negative determination to entire positivity data, whereas the false positive rate is a proportion of positive determination to entire negativity data.

The first threshold TH1 is a threshold for the purpose of holding down the false negative rate of the falling asleep prediction model to equal to or less than a certain level. The second threshold TH2 is a threshold for the purpose of holding down the false positive rate of the falling asleep prediction model to equal to or less than a certain level, and is larger than the first threshold TH1. The first threshold TH1 and the second threshold TH2 are numerical values that can be acquired additionally by performing cross-examination using various thresholds when constructing the falling asleep prediction model by machine learning. In the present embodiment, the storage unit 12 stores the first threshold TH1 and the second threshold TH2 in advance.

The falling asleep time tendency distribution is created based on information such as past activity and sleep information on the subject or a personal opinion of the assistant who assists the subject, and represents with what probability the subject falls asleep in which time band. The falling asleep time tendency distribution may be, for example, simply frequency distribution or probability distribution based on the falling asleep time distribution in a certain period in the past, or may be probability distribution obtained by inputting the body movement data, the heartbeat data, and the breathing data in the daytime into the falling asleep time tendency distribution prediction model that differs from the falling asleep prediction model. The falling asleep time tendency distribution prediction model is generated by machine learning, and is stored in the storage unit 12 in advance. Note that in the present embodiment, the storage unit 12 may store the falling asleep time tendency distribution in advance.

When the predicted value that is output by the falling asleep prediction model is larger than the threshold calculated by the threshold adjustment unit 102, the falling asleep prediction unit 101 determines that the falling asleep sign of the subject is detected, that is, the subject falls asleep after the predetermined time.

When the falling asleep prediction unit 101 detects the falling asleep sign of the subject, the notification processing unit 103 performs the notification processing to the subject or the assistant.

Note that in the present embodiment, the falling asleep prediction device 1 may include the measurement device 2. In this case, the falling asleep prediction device 1 is disposed in a room in which the subject is present, and a terminal device disposed in a room in which the assistant is present has a function of the display unit 14. Also, in the present embodiment, the falling asleep prediction device 1 may be a server. In this case, the terminal device disposed in the room in which the assistant is present has the function of the display unit 14.

Subsequently, an overall operation of the falling asleep prediction device 1 according to the present embodiment will be described with reference to the flowchart of FIG. 2.

Figure 2:
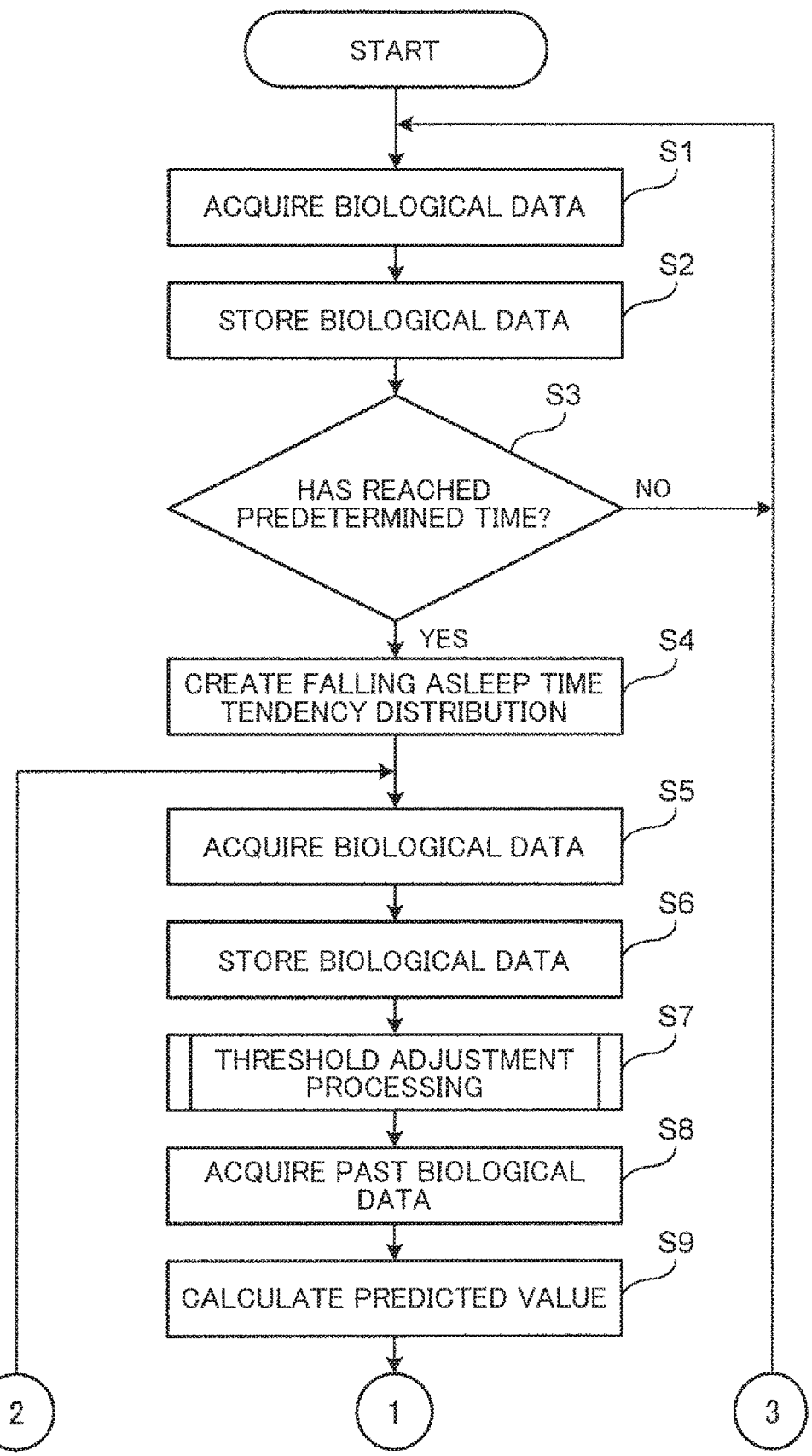
FIG. 2 is a first flowchart for describing an overall operation of a falling asleep prediction device according to the present embodiment.
Figure 3:
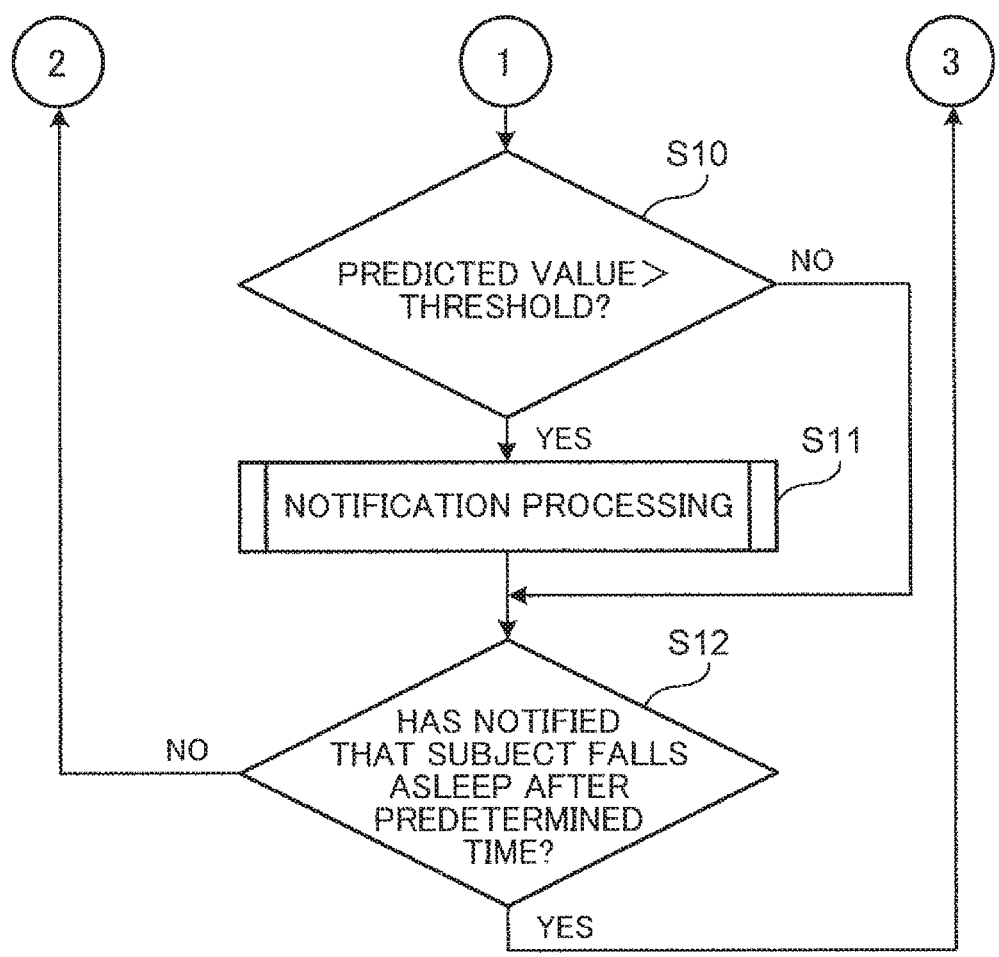
FIG. 3 is a second flowchart for describing the overall operation of the falling asleep prediction device according to the present embodiment.

FIG. 2 is a first flowchart for describing the overall operation of the falling asleep prediction device according to the present embodiment. FIG. 3 is a second flowchart for describing the overall operation of the falling asleep prediction device according to the present embodiment.

First, the biological data acquisition unit 11 acquires the biological data from the measurement device 2 regularly or irregularly (step S1). In the present embodiment, as one example, the biological data acquisition unit 11 acquires the body movement data, the heartbeat data, and the breathing data every second from the measurement device 2.

Next, the biological data acquisition unit 11 stores the acquired biological data in the storage unit 12 (step S2). In the present embodiment, as one example, the biological data acquisition unit 11 stores one-minute averages of the body movement data, the heartbeat data, and the breathing data every minute in the storage unit 12.

The falling asleep prediction unit 101 determines whether the current time has reached predetermined time (step S3). Note that the predetermined time is, for example, supper finish time set by the facility. The predetermined time is, for example, 18:00. The predetermined time is one example, and appropriate time is set according to the subject. When it is determined here that the current time has not reached the predetermined time (NO in step S3), the process returns to step S1.

On the other hand, when it is determined that the current time has reached the predetermined time (YES in step S3), the threshold adjustment unit 102 creates the falling asleep time tendency distribution of the subject (step S4). The threshold adjustment unit 102 creates the falling asleep time tendency distribution, for example, by inputting the body movement data, the heartbeat data, and the breathing data in the daytime from 7:00 to 18:00 into the falling asleep time tendency distribution prediction model, and by obtaining the falling asleep time tendency distribution that is output from the falling asleep time tendency distribution prediction model. The threshold adjustment unit 102 stores the created falling asleep time tendency distribution in the storage unit 12. Note that when the storage unit 12 stores the falling asleep time tendency distribution in advance, the process of step S4 is omitted.

Next, the biological data acquisition unit 11 acquires the biological data from the measurement device 2 (step S5). In the present embodiment, as one example, the biological data acquisition unit 11 acquires the body movement data, the heartbeat data, and the breathing data every second from the measurement device 2.

Next, the biological data acquisition unit 11 stores the acquired biological data in the storage unit 12 (step S6). In the present embodiment, as one example, the biological data acquisition unit 11 stores one-minute averages of the body movement data, the heartbeat data, and the breathing data every minute in the storage unit 12.

Next, at predetermined timing (for example, at one-minute intervals), the threshold adjustment unit 102 performs threshold adjustment processing for calculating the threshold to be used for the falling asleep prediction processing at the current time (step S7). Note that the threshold adjustment processing will be described later.

Next, the falling asleep prediction unit 101 acquires from the storage unit 12 the past biological data for predetermined time from the current time (step S8). For example, the falling asleep prediction unit 101 acquires from the storage unit 12 the past body movement data, the heartbeat data, and the breathing data for one hour from the current time.

Next, the falling asleep prediction unit 101 calculates the predicted value by inputting the acquired biological data into the falling asleep prediction model and obtaining the predicted value that is output from the falling asleep prediction model (step S9).

Note that the time interval at which the threshold setting processing is performed by the threshold adjustment unit 102 may be the same as the time interval at which the predicted value is calculated by the falling asleep prediction unit 101, and may be longer than the time interval at which the predicted value is calculated. That is, for example, the time interval at which the threshold setting processing is performed may be the same one-minute interval as the time interval at which the predicted value is calculated, and may be 30-minute interval that is longer than the time interval at which the predicted value is calculated.

The threshold adjustment unit 102 may perform the threshold setting processing at predetermined time (for example, 18:00) only once a day, calculate the threshold at every predetermined time after 18:00 (for example, every minute), and store the threshold calculated at each predetermined time in the storage unit 12.

Here, the processing for the falling asleep prediction unit 101 to calculate the predicted value will be described more specifically.

The falling asleep prediction unit 101 performs processing for determining the falling asleep sign of the subject from the body movement data, the heartbeat data, and the breathing data recorded in the storage unit 12.

FIG. 4 is a diagram showing one example of the body movement data, the breathing data, and the heartbeat data in the present embodiment. In the present embodiment, as shown in FIG. 4, each measurement data of the body movement data, the heartbeat data, and the breathing data to be used for input has two-dimensional values, and six-dimensional biological data is recorded every minute. That is, the body movement signal that is output from the Doppler sensor of the measurement device 2 is separated into a body movement I signal and a body movement Q signal by I/Q detection that is one type of signal processing. Furthermore, a breathing I signal, a breathing Q signal, a heartbeat I signal, and a heartbeat Q signal are measured by filtering the body movement I signal and the body movement Q signal.

The falling asleep prediction unit 101 acquires the biological data for one hour from the current time from the storage unit 12 at predetermined timing, inputs the biological data into the falling asleep prediction model, and obtains the predicted value.

For example, when the current time is 19:00, the falling asleep prediction unit 101 acquires the biological data from 18:00 to 18:59 from the storage unit 12, and inputs the biological data into the falling asleep prediction model. With respect to the input, the falling asleep prediction model outputs the predicted value that is represented by a real value between 0 and 1 inclusive, and indicates probability of falling asleep within 30 minutes from the current time.

Figure 5:
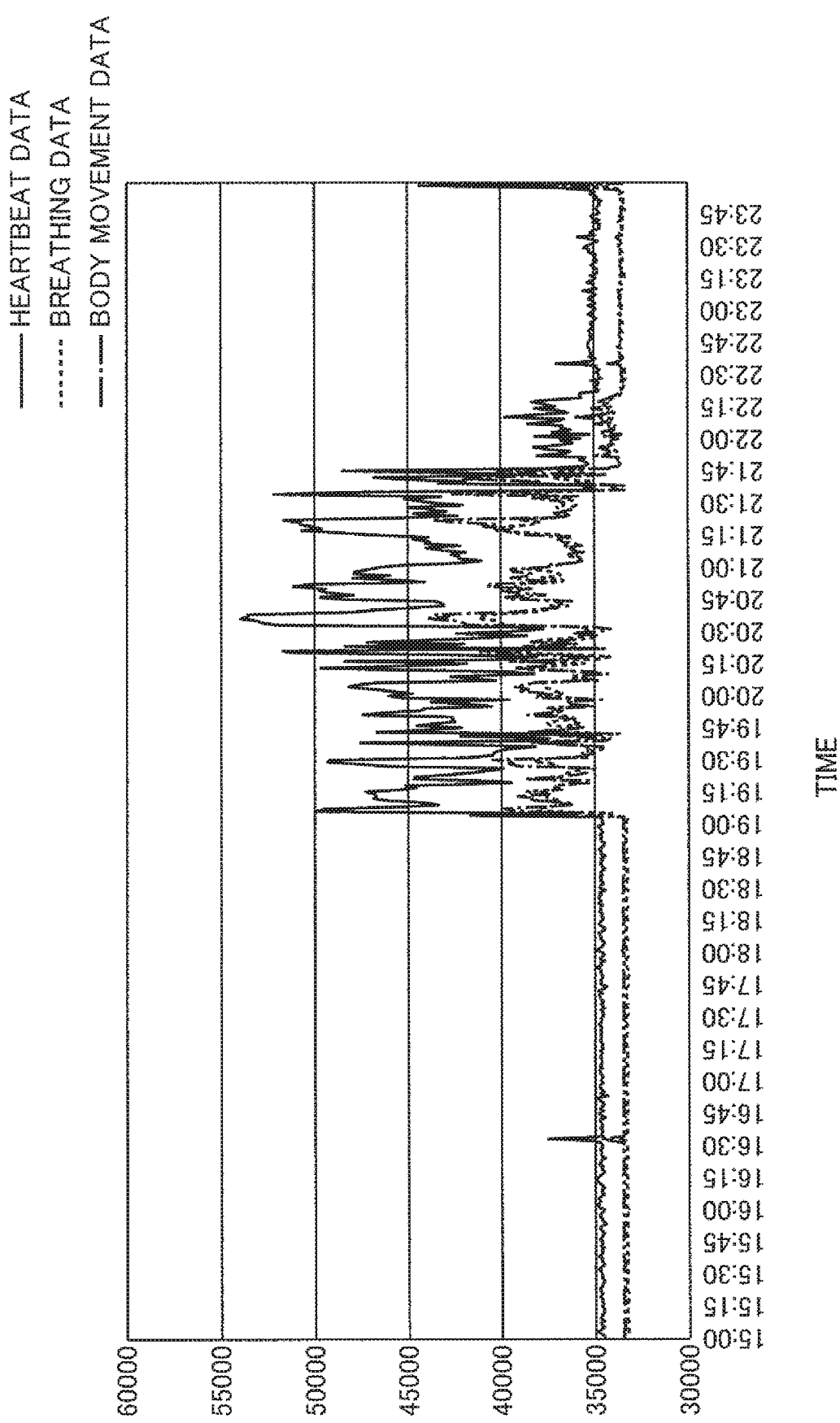
FIG. 5 is a diagram showing one example of waveforms of the body movement data, the heartbeat data, and the breathing data recorded in a storage unit in the present embodiment.
Figure 6:
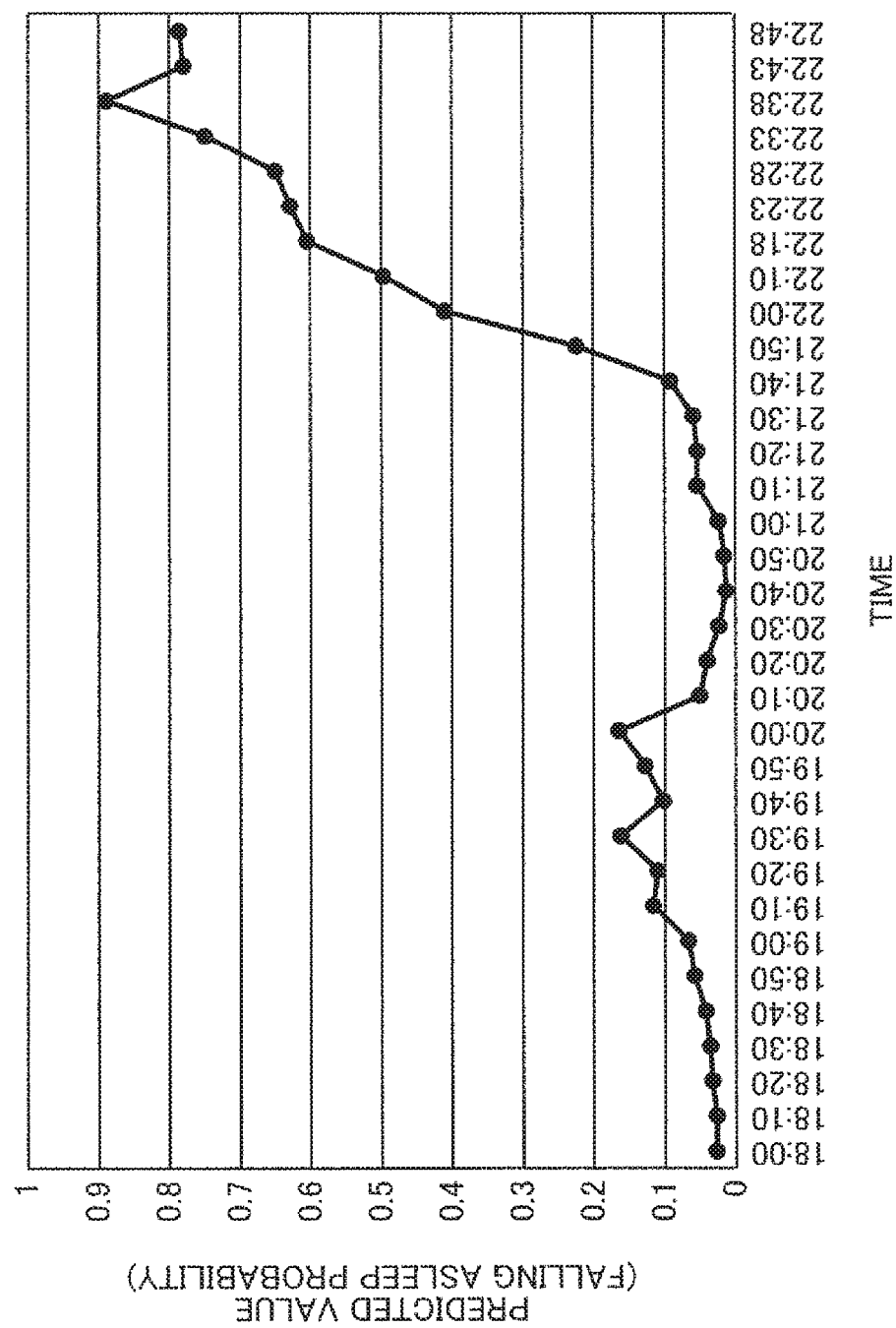
FIG. 6 is a diagram showing one example of a change in a predicted value output by a falling asleep prediction model with respect to biological data after 18:00 in the present embodiment.

FIG. 5 is a diagram showing one example of waveforms of the body movement data, the heartbeat data, and the breathing data recorded in the storage unit 12 in the present embodiment. FIG. 6 is a diagram showing one example of a change in the predicted value output by the falling asleep prediction model with respect to the biological data after 18:00 in the present embodiment. Note that in FIG. 5, the body movement data represents an average of the body movement I signal and the body movement Q signal, the heartbeat data represents an average of the heartbeat I signal and the heartbeat Q signal, and the breathing data represents an average of the breathing I signal and the breathing Q signal.

According to the waveforms shown in FIG. 5, it is considered that the subject has entered the room at around 19:00, activity becomes moderate at around 21:30, and the subject has fallen asleep at about 22:30 to 23:00. As shown in FIG. 6, the predicted value output by the falling asleep prediction model gradually rises from around 22:00 after the activity of the subject becomes moderate, and peaks at around 22:30.

Returning to FIG. 3, next, the falling asleep prediction unit 101 determines whether the calculated predicted value is larger than the threshold calculated by the threshold adjustment unit 102 (step S10). Here, when it is determined that the predicted value is equal to or less than the threshold (NO in step S10), the process returns to step S5.

On the other hand, when it is determined that the predicted value is larger than the threshold (YES in step S10), the notification processing unit 103 performs the notification processing for notifying the assistant that the subject falls asleep after the predetermined time, or for confirming with the subject whether to receive the falling asleep assistance (step S11).

Next, the notification processing unit 103 determines whether the assistant has been notified that the subject falls asleep after the predetermined time (step S12). Here, when it is determined that the assistant has not been notified that the subject falls asleep after the predetermined time (NO in step S12), the process returns to step S5.

On the other hand, when it is determined that the assistant has been notified that the subject falls asleep after the predetermined time (YES in step S12), the process returns to step S1.

Subsequently, the threshold adjustment processing performed by the threshold adjustment unit 102 will be described with reference to FIG. 4. In the threshold adjustment processing, the threshold adjustment unit 102 sets the threshold to be used for the falling asleep prediction processing by using the first threshold TH1, the second threshold TH2, and the falling asleep time tendency distribution.

Figure 7:
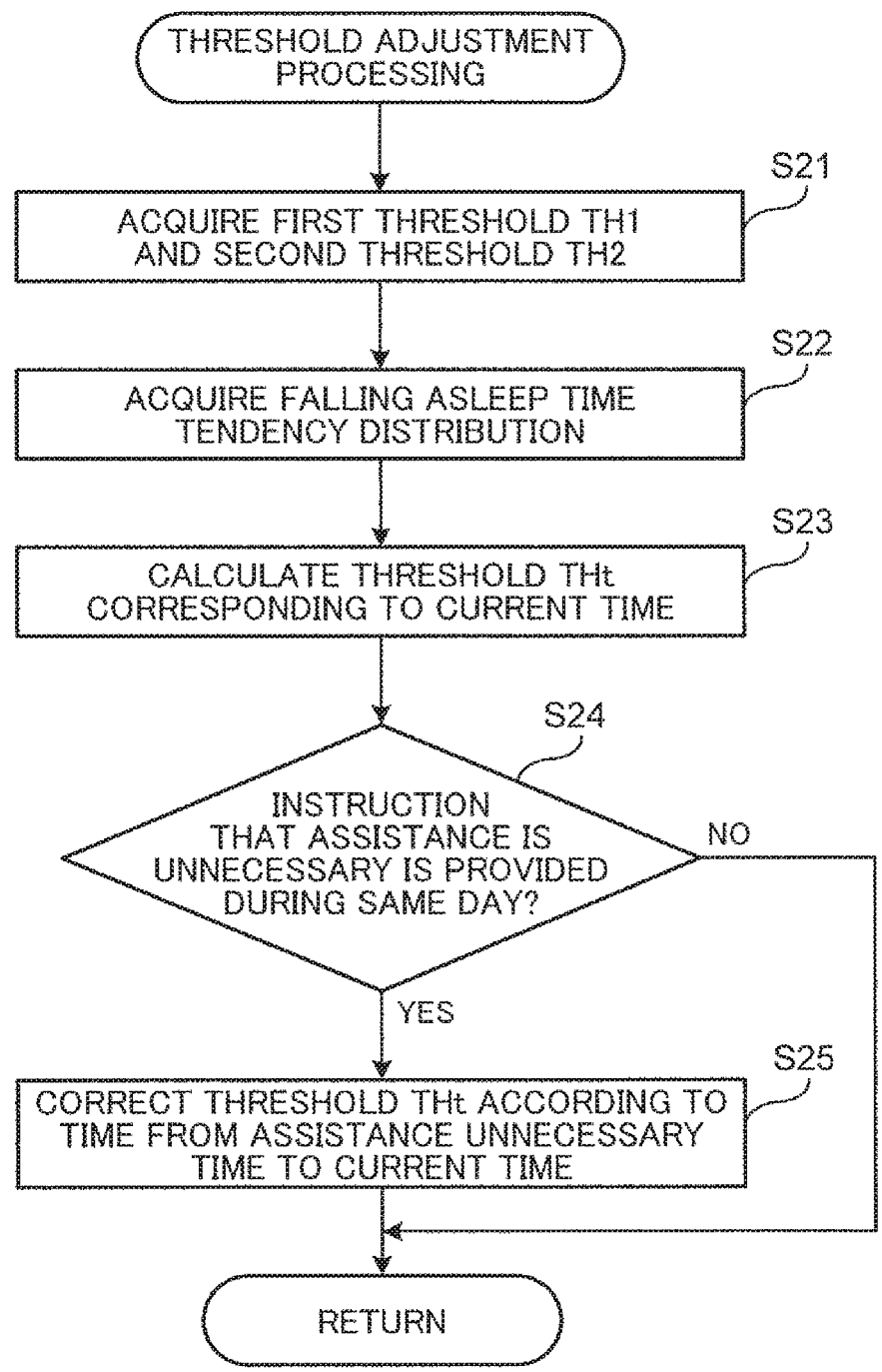
FIG. 7 is a flowchart for describing threshold adjustment processing in step S7 of FIG. 2.

FIG. 7 is a flowchart for describing the threshold adjustment processing in step S7 of FIG. 2.

First, the threshold adjustment unit 102 acquires the first threshold TH1 and the second threshold TH2 from the storage unit 12 (step S21).

Next, the threshold adjustment unit 102 acquires the falling asleep time tendency distribution from the storage unit 12 (step S22).

Figure 8:
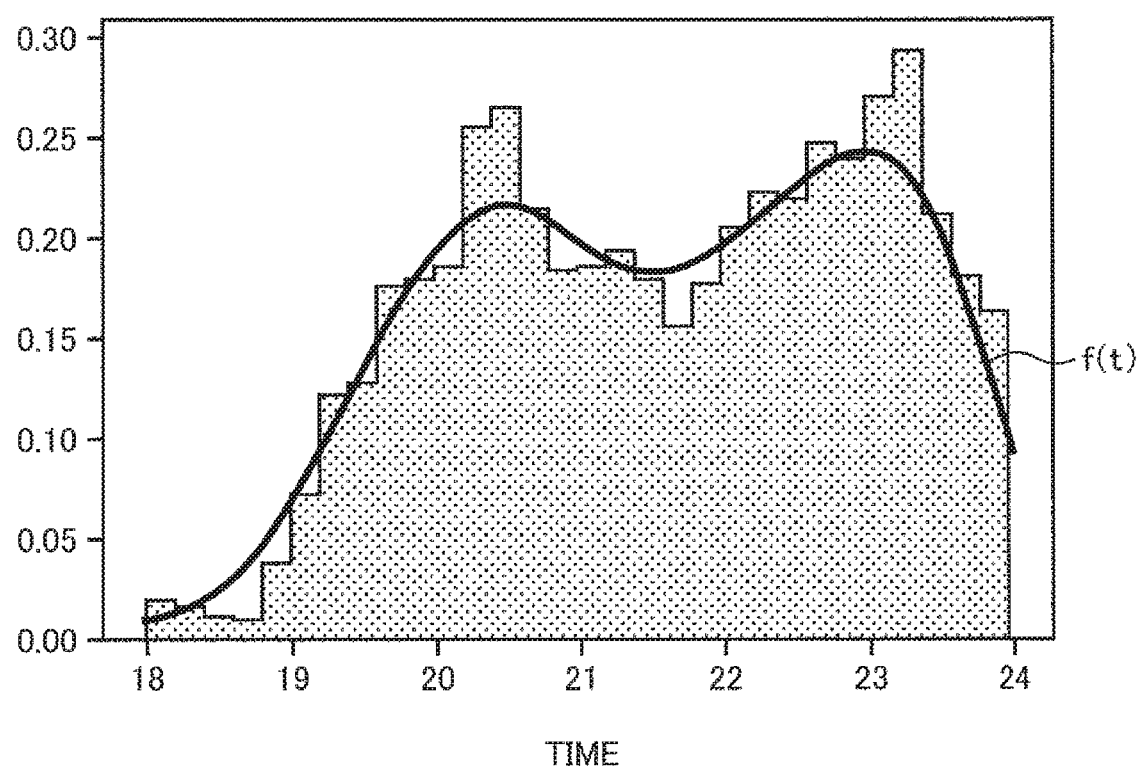
FIG. 8 is a diagram showing one example of falling asleep time tendency distribution to be used in the present embodiment.

FIG. 8 is a diagram showing one example of the falling asleep time tendency distribution to be used in the present embodiment. The falling asleep time tendency distribution is a histogram indicating past falling asleep time distribution of the subject, or a probability density function f(t) generated by kernel density estimation from the past falling asleep time of the subject. Either one may be used depending on intervals of timing to perform the threshold adjustment processing. The range in the horizontal axis of the histogram is from 18:00 to 24:00 in FIG. 8, but the range may be changed in accordance with the falling asleep time tendency of the subject. Distribution generated by another method may be used if the distribution indicates the falling asleep time tendency.

Returning to FIG. 7, next, the threshold adjustment unit 102 calculates a threshold THt corresponding to the current time t (step S23). The threshold adjustment unit 102 calculates the threshold THt that becomes close to the first threshold TH1 as the current time t is time with more tendency to fall asleep, and becomes close to the second threshold TH2 as the current time t is time with less tendency to fall asleep. When using the probability density function f(t) of FIG. 8 for the falling asleep time tendency distribution, the threshold adjustment unit 102 calculates the threshold THt corresponding to each time t by the following formula (1). Note that in formula (1), max(f) represents the maximum value of the function f.

[Formula 1]

$$TH_t = \frac{f(t+0.5)}{\max(f)}TH1 + \left(1 - \frac{f(t+0.5)}{\max(f)}\right)TH2 \quad (1)$$

Here, the function is f(t+0.5) because the falling asleep prediction model is designed to output probability of falling asleep within 30 minutes from the current time. The function may be changed according to the design of the falling asleep prediction model. The denominator max(f) is also one example for setting THt=TH1 when the function f is the maximum value, and can be changed as appropriate. By calculating the threshold THt using the formula (1), the threshold THt becomes a low value close to the first threshold TH1 if time in 30 minutes is time with high probability that the subject falls asleep in the past, and the threshold THt becomes a high value close to the second threshold TH2 if time in 30 minutes is time with low probability that the subject falls asleep in the past.

Next, the threshold adjustment unit 102 determines whether an instruction is provided from the subject during the same day that assistance is unnecessary in the notification processing to be described later (step S24). Here, when it is determined that instruction that assistance is unnecessary is not provided during the same day (NO in step S24), the threshold adjustment processing ends.

On the other hand, when it is determined that the instruction that assistance is unnecessary is provided during the same day (YES in step S24), the threshold adjustment unit 102 corrects the threshold THt according to time from assistance unnecessary time when instructed by the subject that assistance is unnecessary to the current time (step S25). The threshold adjustment unit 102 corrects the threshold THt to increase more as the time from the assistance unnecessary time to the current time decreases. This allows reduction in a frequency with which unnecessary assistance preliminary announcement is generated at time close to the assistance unnecessary time. As the correction method, for example, the value of the function f is changed, and the threshold adjustment unit 102 increases the threshold THt by setting the function f to 0 within 30 minutes from the assistance unnecessary time and reducing the function f by half from 30 minutes to 60 minutes after the assistance unnecessary time. Instead of the threshold adjustment unit 102 increasing the threshold THt, the falling asleep prediction unit 101 may not perform falling asleep prediction itself within certain time (for example, 30 minutes) from the assistance unnecessary time.

Subsequently, the notification processing performed by the notification processing unit 103 will be described with reference to a flowchart of FIG. 9.

Figure 9:
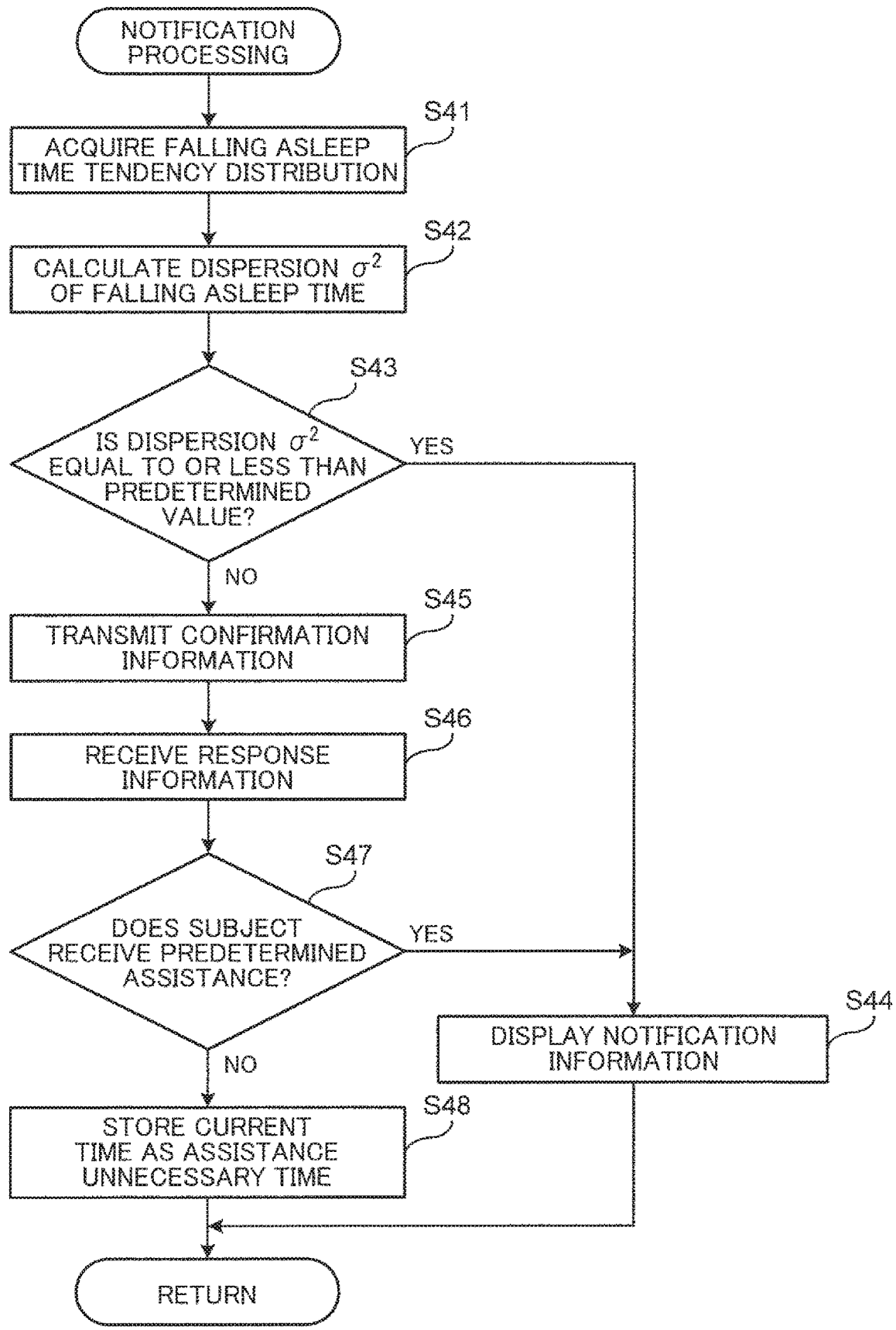
FIG. 9 is a flowchart for describing notification processing in step S11 of FIG. 3.

FIG. 9 is a flowchart for describing the notification processing in step S11 of FIG. 3.

First, the notification processing unit 103 acquires the falling asleep time tendency distribution of the subject from the storage unit 12 (step S41).

Next, the notification processing unit 103 calculates dispersion $\sigma^2$ of the falling asleep time from the acquired falling asleep time tendency distribution (step S42).

Next, the notification processing unit 103 determines whether the dispersion $\sigma^2$ is equal to or less than a predetermined value (step S43). The dispersion $\sigma^2$ of the falling asleep time represents variation magnitude of the falling asleep time. Therefore, when the dispersion $\sigma^2$ is small, the falling asleep time is constant and the subject falls asleep almost at the same time every day. On the other hand, when the dispersion $\sigma^2$ is large, the falling asleep time is not constant and the falling asleep time has a great variation. Here, when it is determined that the dispersion $\sigma^2$ is equal to or less than the predetermined value (YES in step S43), the notification processing unit 103 displays, on the display unit 14, the notification information for notifying that the subject falls asleep after the predetermined time (step S44). Through display of the notification information, the assistant is notified that the subject falls asleep after the predetermined time. By checking the notification information displayed on the display unit 14, the assistant provides the predetermined assistance before the subject falls asleep.

On the other hand, when it is determined that the dispersion $\sigma^2$ is larger than the predetermined value (NO in step S43), the notification processing unit 103 transmits the confirmation information for confirming with the subject whether to receive the predetermined assistance to the assistance preliminary announcement device 3 (step S45). The communication unit 31 of the assistance preliminary announcement device 3 receives the confirmation information. The assistance confirmation processing unit 301 generates a confirmation screen for confirming with the subject whether to receive the predetermined assistance, and displays the generated confirmation screen on the display unit 33. Note that the assistance confirmation processing unit 301 may output the confirmation information by voice. Then, the input unit 34 receives input by the subject about whether to receive the predetermined assistance. The communication unit 31 transmits the response information indicating whether the subject receives the predetermined assistance to the falling asleep prediction device 1.

Next, the communication unit 15 receives the response information transmitted by the assistance preliminary announcement device 3 (step S46).

Next, based on the received response information, the notification processing unit 103 determines whether the subject receives the predetermined assistance (step S47). Here, when it is determined that the subject receives the predetermined assistance (YES in step S47), the process proceeds to step S44, and the notification processing unit 103 displays, on the display unit 14, the notification information for notifying that the subject falls asleep after the predetermined time.

On the other hand, when it is determined that the subject does not receive the predetermined assistance, that is, when it is determined that the instruction is provided that assistance is unnecessary (NO in step S47), the notification processing unit 103 stores, in the storage unit 12, the current time as the assistance unnecessary time when instructed that assistance is unnecessary (step S48). The assistance unnecessary time stored in the storage unit 12 is used for correction of the threshold by the threshold adjustment unit 102 as described above.

Note that in step S46, when the response information is not received even if the predetermined time elapses, that is, when there is no response about whether the subject receives the predetermined assistance, the process of step S48 may be performed.

The dispersion $\sigma^2$ of the falling asleep time represents the variation magnitude of the falling asleep time in the present embodiment, but the present disclosure is not particularly limited to this example. Standard deviation of the falling asleep time may represent the variation magnitude of the falling asleep time.

For the subject who has difficulty or cannot respond to whether to receive the predetermined assistance for reasons such as a cognitive function disorder, the notification information may be unconditionally displayed on the display unit 14 without transmitting the confirmation information by setting in advance.

Before the assistance preliminary announcement device 3 displays the confirmation information, the subject may perform an operation of actively requesting the predetermined assistance on the input unit 34, the communication unit 31 may transmit information requesting the predetermined assistance to the falling asleep prediction device 1, and the display unit 14 of the falling asleep prediction device 1 may display the information requesting the predetermined assistance.

In the present disclosure, all or part of units, devices, members, or parts, or all or part of functional blocks of the block diagram shown in the diagrams may be executed by one or more electronic circuits including a semiconductor device, a semiconductor integrated circuit (IC), or large scale integration (LSI). The LSI or IC may be integrated into one chip, and may be configured through combination of two or more chips. For example, functional blocks other than a storage device may be integrated into one chip. The integrated circuit that is called LSI or IC here is also called differently depending on degree of integration, and may be called a system LSI, very large scale integration (VLSI), or ultra large scale integration (VLSI). A field programmable gate array (FPGA) that is programmed after manufacture of the LSI, or a reconfigurable logic device that allows reconfiguration of connection inside the LSI or setup of circuit blocks inside the LSI can be used for the same purpose.

Furthermore, all or part of functions or operations of units, devices, members, or parts can be executed by software processing. In this case, the software is recorded in a non-transitory recording medium, such as one or more ROMs, optical disks, or hard disk drives. When the software is executed by a processor, the functions specified by the software are executed by the processor and a peripheral device. The system or device may include the one or more non-transitory recording media that record the software, the processor, and necessary hardware devices, for example, an interface.

The information processing device, the information processing method, and the computer-readable recording medium recording the information processing program according to the present disclosure, which can predict when the subject falls asleep before falling asleep, are useful as the information processing device, the information processing method, and the computer-readable recording medium recording the information processing program that predict that the subject falls asleep before the subject falls asleep.

This application is based on Japanese Patent application No. 2018-139182 filed in Japan Patent Office on Jul. 25, 2018, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

The invention claimed is:

1. An information processing device comprising:
   an acquisition unit configured to acquire biological information on a subject;
   a prediction unit configured to predict that the subject falls asleep after a specified time from the current time by using the biological information; and
   a notification unit configured to notify that the subject falls asleep after the specified time.

2. The information processing device according to claim 1, wherein the acquisition unit acquires the biological information from a sensor that measures the biological information from the subject in a non-contact manner.

3. The information processing device according to claim 2, wherein the sensor is a radio Doppler sensor.

4. The information processing device according to claim 1, wherein the biological information includes body movement data indicating body movement of the subject, breathing data indicating breathing of the subject, and heartbeat data indicating heartbeat of the subject.

5. The information processing device according to claim 1, further comprising a storage unit configured to store a falling asleep prediction model constructed by machine learning using the biological information as an input value and a predicted value indicating probability that the subject falls asleep in the future after the specified time from the current time as an output value,
   wherein the prediction unit determines whether the predicted value obtained by inputting the biological information into the falling asleep prediction model is larger than a threshold, and when it is determined that the predicted value is larger than the threshold, the prediction unit determines that the subject falls asleep after the specified time.

6. The information processing device according to claim 5, further comprising a threshold adjustment unit configured to adjust the threshold based on past falling asleep time tendency distribution of the subject.

7. The information processing device according to claim 1, wherein the notification unit determines whether variation magnitude of past falling asleep time of the subject is equal to or less than a predetermined value, and when it is determined that the variation magnitude is equal to or less than the predetermined value, the notification unit notifies that the subject falls asleep after the specified time.

8. The information processing device according to claim 7, wherein the subject is a person to be assisted who receives predetermined assistance immediately before falling asleep, and when it is determined that the variation magnitude is larger than the predetermined value, the notification unit transmits confirmation information for confirming with the subject whether to receive the predetermined assistance.

9. An information processing method comprising, by a computer:

acquiring biological information on a subject;

predicting that the subject falls asleep after a specified time from the current time by using the biological information; and notifying that the subject falls asleep after the specified time.

10. The information processing device according to claim 1, wherein the prediction unit is configured to use a falling asleep prediction model and the biological information to determine a probability that the subject falls asleep within the specified time from the current time.

11. The information processing device according to claim 1, wherein i) the subject is to receive predetermined assistance from an assistant within the specified time before falling asleep, ii) the prediction unit is configured to predict that the subject falls asleep within the specified time from the current time by using the biological information, and iii) the notification unit configured to notify the assistant to assist the subject with the predetermined assistance within the specified time before falling asleep.

12. The information processing device according to claim 11, wherein the predetermined assistance comprises predetermined assistance in performing one of: tooth brushing, changing clothes, and taking of medication.

13. The information processing device according to claim 1, wherein i) the subject is to receive predetermined assistance from an assistant within the specified time on a day before falling asleep, ii) the prediction unit is configured to determine whether a predicted value obtained by inputting the biological information into a falling asleep prediction model is larger than a threshold, and when it is determined that the predicted value is larger than the threshold, the prediction unit determines that the subject falls asleep after the specified time, iii) the device further comprises a threshold adjustment unit configured to calculate the threshold corresponding to the current time, iv) the threshold adjustment unit determines whether an instruction is provided from the subject during the same day that assistance is unnecessary, and v) when the threshold adjustment unit determines that the instruction that assistance is unnecessary is provided during the same day, the threshold adjustment unit corrects the threshold according to the time from when the subject provides the instruction that assistance is unnecessary to the current time.

14. The information processing device according to claim 1, wherein i) the notification unit determines whether the subject receives predetermined assistance from an assistant within the specified time before falling asleep, ii) when the notification unit determines that the subject receives the predetermined assistance, the notification unit displays, on a display, notification information providing a notification that the subject falls asleep after the specified time, and iii) when the notification unit determines that the subject does not receive the predetermined assistance because the subject provides an instruction that assistance is unnecessary, the notification unit stores, in a storage unit, the current time as the assistance unnecessary time when instructed that assistance is unnecessary.

15. A computer-readable recording medium recording an information processing program that causes a computer to function as:

an acquisition unit configured to acquire biological information on a subject;

a prediction unit configured to predict that the subject falls asleep after a specified time from the current time by using the biological information; and a notification unit configured to notify that the subject falls asleep after the specified time.

* * * * *